United States Patent
Uchida et al.

(10) Patent No.: US 7,389,677 B2
(45) Date of Patent: Jun. 24, 2008

(54) MEASURING METHOD AND DEVICE FOR LIQUID CRYSTAL VISCOSITY COEFFICIENT

(75) Inventors: Tatsuo Uchida, Sendai (JP); Tetsuya Miyashita, Sendai (JP); Takahiro Ishinabe, Sendai (JP)

(73) Assignees: Tohoku Techno-Brains Corporation, Miyagi (JP); Aomori Support Center for Industrial Promotion, Aomori (JP)

( * ) Notice: Subject to any disclaimer, the term of this patent is extended or adjusted under 35 U.S.C. 154(b) by 0 days.

(21) Appl. No.: 10/553,180

(22) PCT Filed: Oct. 5, 2004

(86) PCT No.: PCT/JP2004/014627

§ 371 (c)(1),
(2), (4) Date: Aug. 7, 2006

(87) PCT Pub. No.: WO2005/036137

PCT Pub. Date: Apr. 21, 2005

(65) Prior Publication Data

US 2006/0272395 A1    Dec. 7, 2006

(30) Foreign Application Priority Data

Oct. 10, 2003    (JP)    ................ 2003-351688

(51) Int. Cl.
*G01N 11/00*    (2006.01)

(52) U.S. Cl. ...................... 73/54.01; 73/54.02

(58) Field of Classification Search ................ 73/54.01, 73/54.02
See application file for complete search history.

(56) References Cited

U.S. PATENT DOCUMENTS

| | | | | |
|---|---|---|---|---|
| 6,266,109 | B1 * | 7/2001 | Yamaguchi et al. | ........... 349/86 |
| 6,774,977 | B1 * | 8/2004 | Walton et al. | ............... 349/177 |
| 6,885,412 | B2 * | 4/2005 | Ohnishi et al. | ................. 349/72 |
| 7,084,939 | B2 * | 8/2006 | Paukshto et al. | ............ 349/101 |
| 7,154,463 | B2 * | 12/2006 | Kwag | ........................... 345/94 |

FOREIGN PATENT DOCUMENTS

JP    2004-20255    *    1/2004

* cited by examiner

*Primary Examiner*—Helen C. Kwok
(74) *Attorney, Agent, or Firm*—Young & Thompson

(57) ABSTRACT

In a measuring method for determining values of viscosity coefficients of a liquid crystal by fitting Ericksen-Leslie theoretical values to measured response characteristics, in the first step, ON response characteristics of a liquid crystal cell 10 with homogeneous alignment are initially measured, and a value of a rotational viscosity coefficient $\gamma_1$ is determined from the measured ON response characteristics. Then, in the second step, OFF response characteristics are measured, and values of Miesovicz shear viscosity coefficients $\eta_1$ and $\eta_2$ are determined from the measured OFF response characteristics. In the calculation in the first step, the viscosity coefficients other than $\gamma_1$ are assigned general values. In the calculation in the second step, $\gamma_1$ is assigned the value determined in the first step.

3 Claims, 5 Drawing Sheets

TIME (ms)
(ON RESPONSE)

TIME (ms)
(OFF RESPONSE)

MEASURING METHOD AND DEVICE FOR LIQUID CRYSTAL VISCOSITY COEFFICIENT

TECHNICAL FIELD

The present invention relates to methods and devices for measuring viscosity coefficients of a liquid crystal, and specifically to a method and device capable of measuring a rotational viscosity coefficient $\gamma_1$, and $\eta_1$ and $\eta_2$ of Miesovicz viscosity coefficients of a liquid crystal, with a high degree of accuracy.

BACKGROUND ART

With recent advances in liquid crystal televisions, there are strong demands for the development of liquid crystal displays (hereinafter may be simply referred to as "LCDs") capable of performing higher-speed switching. The present inventors have revealed that a flow effect of liquid crystal plays an important role in the LCD response (S. Onda, T. Miyashita, T. Uchida: Asia Display 98 Proceedings (1998) p. 1055). The theory of flow effect was developed by Ericksen-Leslie (F. M. Leslie: Quart. J. Mech, Appl. Math., 19 (1966) p. 357; F. M. Leslie: Liquid Crystals (1968) p. 365; and J. L. Ericksen: Mol. Cryst. Liq. Cryst. (1969) p. 153). According to this theory, based on the assumption that liquid crystal is an anisotropic viscous fluid, a fluid dynamical system incorporating the theory of continuous elastic bodies can be described by the equation of motion shown in Equation 1 and the conservation of angular momentum equation shown in Equation 2 (C. Z. van Doorn: J. of Applied Physics, 46, 9 (1975) p. 3738).

[Equation 1]

Equation of Motion $$\frac{d}{dz}\begin{Bmatrix} \alpha_2 n_x^{\&} n_z + \alpha_3 n_z^{\&} n_x + \\ \left(\alpha_1 n_x n_y n_z^2 + \frac{1}{2}\alpha_3 n_x n_y + \frac{1}{2}\alpha_6 n_x n_y\right)\frac{\partial v_y}{\partial z} + \\ \frac{1}{2}(2\alpha_1 n_x^2 n_z^2 - \alpha_2 n_z^2 + \alpha_3 n_x^2 + \\ \alpha_4 + \alpha_5 n_z^2 + \alpha_6 n_x^2)\frac{\partial v_x}{\partial z} \end{Bmatrix} = 0$$

$$\frac{d}{dz}\begin{Bmatrix} \alpha_2 n_y^{\&} n_z + \alpha_3 n_z^{\&} n_y + \\ \left(\alpha_1 n_x n_y n_z^2 + \frac{1}{2}\alpha_3 n_x n_y + \frac{1}{2}\alpha_6 n_x n_y\right)\frac{\partial v_x}{\partial z} \\ +\frac{1}{2}(2\alpha_1 n_y^2 n_z^2 - \alpha_2 n_z^2 + \alpha_3 n_y^2 + \\ \alpha_4 + \alpha_5 n_z^2 + \alpha_6 n_y^2)\frac{\partial v_y}{\partial z} \end{Bmatrix} = 0$$

$\alpha_1$ to $\alpha_6$: Leslie viscosity coefficients
v: velocity vector
n: alignment vector

[Equation 2]

Equation of Conservation of Angular Momentum $$\gamma_1 n_x^{\&} = \gamma n_x - \frac{\partial F}{\partial n_x} + \frac{\partial}{\partial z}\frac{\partial F}{\partial\left(\frac{\partial n_x}{\partial z}\right)} - \alpha_2 n_z \frac{\partial v_x}{\partial z}$$

$$\gamma_1 n_y^{\&} = \gamma n_y - \frac{\partial F}{\partial n_y} + \frac{\partial}{\partial z}\frac{\partial F}{\partial\left(\frac{\partial n_y}{\partial z}\right)} - \alpha_2 n_z \frac{\partial v_y}{\partial z}$$

$$\gamma_1 n_z^{\&} = \gamma n_z - \frac{\partial F}{\partial n_z} + \frac{\partial}{\partial z}\frac{\partial F}{\partial\left(\frac{\partial n_z}{\partial z}\right)} -$$

$$\varepsilon_0 \Delta\varepsilon\left(\frac{D_z}{n_z^2(\varepsilon_{//}-\varepsilon_\perp)+\varepsilon_\perp}\right)^2 n_z - \alpha_3 n_x \frac{\partial v_x}{\partial z} - \alpha_3 n_y \frac{\partial v_y}{\partial z}$$

$\gamma_1$: rotational viscosity coefficient ($\gamma_1 = \alpha_3 - \alpha_2$)
$\gamma$: arbitrary constant
$D_z$: electric flux density
$\varepsilon_{//}$: permittivity along the major axis
$\varepsilon_\perp$: permittivity along the minor axis
F: free energy density of distortion $$F = \frac{1}{2}k_{11}\left(\Delta_{//}\vec{n}\right)^2 + \frac{1}{2}k_{22}\left(\vec{n}_{//}(\nabla\times\vec{n}) + \frac{\pi}{\lambda_0}\right)^2 + \frac{1}{2}k_{33}(\vec{n}\times(\nabla\times\vec{n}))^2$$

$k_{11}, k_{22}, k_{33}$: elastic constants
$\lambda_0$: helical pitch

Coefficients $\alpha_1$ to $\alpha_6$ included in Equation 1 and Equation 2 described above are called Leslie viscosity coefficients. Since there is a relationship $\alpha_6 = \alpha_2 + \alpha_3 + \alpha_5$ among these coefficients, five coefficients out of the total of six coefficients are independent. However, they cannot be directly measured in principle, as the correspondence with measuring systems is uncertain. On the other hand, Miesovicz viscosity coefficients are known as viscosity coefficients that are in a certain correspondence with measuring systems (that is, measurable in principle). As shown in FIG. 1, the Miesovicz viscosity coefficients include four coefficients, such as: viscosity coefficients $\eta_1$ and $\eta_2$ (shear viscosity coefficients) with respect to shear flows parallel to the minor axis and the major axis, respectively, of a molecule; a viscosity coefficient $\eta_3$ (twist viscosity coefficient) with respect to flow in twist directions about the major axis of a molecule; and a viscosity coefficient $\eta_{12}$ (compression viscosity coefficient) with respect to flow in directions along which the minor axis of a molecule is compressed. It is known that five parameters, including the rotational viscosity coefficient $\gamma_1$ (this is also measurable) in Equation 2 in addition to the four viscosity coefficients described above, and the Leslie viscosity coefficients $\alpha_1$ to $\alpha_6$ have a relationship that can be expressed as shown in Equation 3. Therefore, if these five parameters can be measured with a high degree of accuracy, the Leslie viscosity coefficients can be determined by Equation 4 solving Equation 3 with respect to $\alpha$. Using this result to solve Equation 1 and Equation 2 by computer numerical solution, a response of a liquid crystal can be properly evaluated, and further, a contribution to improved liquid crystal materials can be made.

$\eta$: Miesovicz viscosity coefficient $\eta_1 = (-\alpha_2 + \alpha_4 + \alpha_5)/2$ $\eta_2 = (\alpha_3 + \alpha_4 + \alpha_6)/2$ $\eta_3 = \alpha_4/2$ $$\eta_{12} = \alpha_1$$

$$\gamma_1 = \alpha_3 - \alpha_2 \qquad \text{[Equation 3]}$$

α: Leslie viscosity coefficient $$\alpha_1 = \eta_{12}$$

$$\alpha_2 = -(\eta_1 - \eta_2 + \gamma_1)/2$$

$$\alpha_3 = -(\eta_1 - \eta_2 - \gamma_1)/2$$

$$\alpha_4 = 2\eta_3$$

$$\alpha_5 = (3\eta_1 + \eta_2 - 4\eta_3 - \gamma_1)/2$$

$$(\alpha_6 = \alpha_2 + \alpha_3 + \alpha_5) \qquad \text{[Equation 4]}$$

A conventionally known method for measuring the viscosity coefficients of a liquid crystal is a method for determining the optimal parameters, using the electrical response characteristics of a twisted nematic (TN) liquid crystal cell, by fitting calculated values obtained by simultaneously varying the above-described five parameters to measured values (O. Cossalter, B. Carmer, D. A. Mlynsky: J. of Physics 2, At. Mol. Cluster Phys. Chem. Phys. Mech. Hydrodyn. Vol. 6, No. 12 (1996) pp. 1663-1669). Since the parameter $\eta_{12}$ related to compression is generally negligible, the number of parameters that are simultaneously varied is normally four. As for the rotational viscosity coefficient $\gamma_1$, there is a known measuring method using a rotational viscometer with a special structure, in which voltages can be applied to two movable surfaces (K. Skarp, S. T. Lagerwall, B. Stebler: "Measurement of hydrodynamic parameters for nematic 5CB", Molecular Crystal Liquid Crystal, Vol. 60 (1980) pp. 215-236).

DISCLOSURE OF INVENTION

Problems to be Overcome by the Invention

However, the conventional measurement by fitting described above has problems in that it requires as much as four parameters simultaneously varied, takes a long time to calculate, and is low in accuracy. Moreover, the measuring method using a rotational viscometer can measure only the rotational viscosity coefficient $\gamma_1$, and its accuracy is insufficient. That is, in the conventional art, there is no established method for measuring the above-described five viscosity coefficients that are dominant factors in determining the LCD response. Therefore, the present invention particularly deals with the rotational viscosity coefficient $\gamma_1$ and the Miesovicz shear viscosity coefficients $\eta_1$ and $\eta_2$ that are dominant factors in determining the response speed, and aims to provide a method and device that are capable of measuring the viscosity coefficients of a liquid crystal, easily and with a high degree of accuracy.

Means for Overcoming the Problems

In the process of intensive research to achieve the object described above, the present inventors have chosen homogeneous alignment as the alignment of liquid crystal molecules, studied a fitting method using the electro-optical response characteristics, and found the following. That is, in the homogeneous alignment where the liquid crystal molecules are substantially parallel to the substrates when a low voltage is applied, the twist viscosity coefficient has no effect and the shear viscosity coefficients have virtually no effect on the change of alignment when a voltage is applied across the two substrates. Therefore, the response characteristics when the applied voltage is switched from low to high levels are less subject to $\eta_1$ and $\eta_2$ compared with the cases of other alignment modes. That is, using the response characteristics (ON response characteristics) when the applied voltage is changed from a low voltage (such as 0 V) to a high voltage (such as 10 V), the rotational viscosity coefficient $\gamma_1$ only can be determined under conditions where the Miesovicz shear viscosity coefficients $\eta_1$ and $\eta_2$ and the twist viscosity coefficient $\eta_3$ have virtually no effect. The compression parameter $\eta_{12}$ is negligible as described above (the same applies to the following). In addition, the Miesovicz shear viscosity coefficients $\eta_1$ and $\eta_2$ can be determined using the response characteristics (OFF response characteristics) when the applied voltage is changed from a high voltage (such as 10 V) to a low voltage (such as 0 V). The twist viscosity coefficient $\eta_3$, which has no effect thereon, can also be negligible in this case.

The present invention has been made based on the finding described above, and can be summarized as follows.

(1) A measuring method for determining values of viscosity coefficients of a liquid crystal by fitting Ericksen-Leslie theoretical values to measured response characteristics, the measuring method including the steps of measuring ON response characteristics of a liquid crystal cell with homogeneous alignment; determining a value of a rotational viscosity coefficient $\gamma_1$ from the measured ON response characteristics; measuring OFF response characteristics of the liquid crystal cell; and determining values of Miesovicz shear viscosity coefficients $\eta_1$ and $\eta_2$ from the measured OFF response characteristics.

(2) A measuring device for determining values of viscosity coefficients of a liquid crystal by fitting Ericksen-Leslie theoretical values to measured response characteristics, the measuring device including a light source illuminating a liquid crystal cell; a voltage supply capable of switching a voltage to be applied to the liquid crystal cell between high and low levels; a transmittance measuring unit capable of collecting transmittance data for light originating from the light source and passing through the liquid crystal cell, at intervals of 100 μs or less, from the switching point at the voltage supply; and an arithmetic unit for determining a value of the rotational viscosity coefficient $\gamma_1$ by fitting the theoretical values calculated on varying $\gamma_1$, to data collected by the transmittance measuring unit when the voltage supply is switched to the high level, and for determining values of the Miesovicz shear viscosity coefficients $\eta_1$ and $\eta_2$ by fitting the theoretical values calculated on varying $\eta_1$ and $\eta_2$ while $\gamma_1$ is fixed at the value previously determined, to data collected by the transmittance measuring unit when the voltage supply is switched to the low level.

Advantages

In the present invention, using electro-optical response characteristics that are less subject to other viscosity coefficients, the 1$^{st}$ fitting for the rotational viscosity coefficient is initially performed, and the 2$^{nd}$ fitting for the shear viscosity coefficients is subsequently performed. This not only greatly improves the accuracy of measurement, but also significantly reduces the time required for calculation, because the number of parameters simultaneously varied is only two at a maximum.

Figure 1:
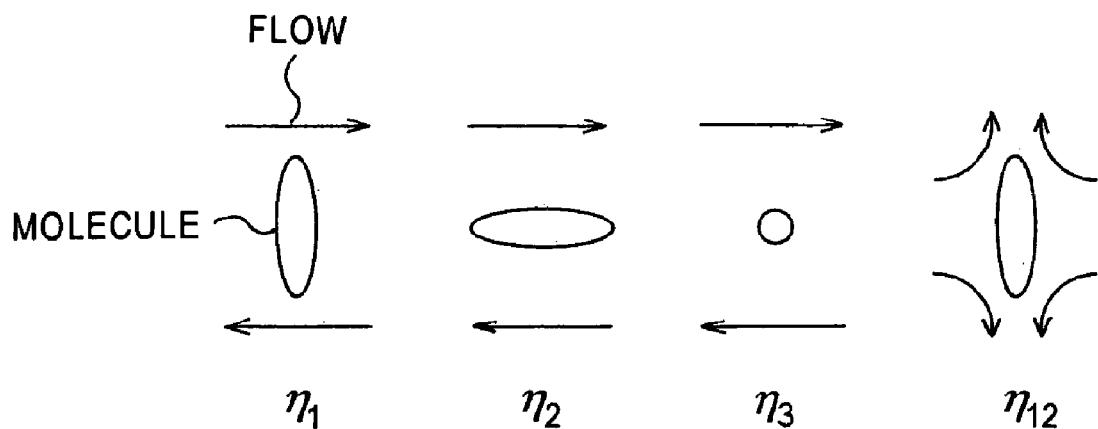
FIG. 1 is a diagram showing the correspondence between the Miesovicz shear viscosity coefficients and the states of flow.

REFERENCE NUMERALS 1 light source
2 voltage supply
3 transmittance measuring unit
4 arithmetic unit
10 liquid crystal cell
11, 12 polarizer

BEST MODE FOR CARRYING OUT THE INVENTION

In the present invention, a liquid crystal cell to be measured has homogeneous alignment. The homogeneous alignment is an alignment where liquid crystal molecules are arranged substantially parallel to the substrates when a low voltage is applied. "Substantially parallel" here means that the major axes of the liquid crystal molecules projected onto a substrate are substantially parallel to one another, and that the tilt angles aligned with the plus or minus direction from the substrate surface range from 0 to 90 degrees. It is preferable that the differences in azimuth angle between molecules be within 10 degrees (preferably 2 degrees) in absolute value. The azimuth angle here means the angle that the major axis of a molecule forms with a reference axis arranged parallel to the substrate surface.

In a liquid crystal cell with homogeneous alignment, the effect of the viscosity coefficients on the ON response characteristics other than that of the rotational viscosity coefficient is so small as to be negligible. Thus, in the first step, in the present invention, the rotational viscosity coefficient $\gamma_1$ is determined by fitting the Ericksen-Leslie theoretical value (hereinafter simply referred to as theoretical value or calculated value) to the result obtained by measuring the ON response characteristics (measured value or experimental value). Although the cell gap of the liquid crystal cell to be measured is not specifically defined, it preferably ranges from 2 to 10 μm so that a change in optical characteristics can be detected as a change in birefringence characteristics or as a change in transmittance.

The ON response characteristics are electro-optical response characteristics at the point of ON switching, that is, when a voltage applied to the liquid crystal cell is switched from a low voltage to a high voltage. The ON response characteristics can be described as a change in the transmittance of the liquid crystal with time elapsed from the ON switching. The high voltage is preferably an alternating voltage of a square wave having a period of 10 ms or less. Although not specifically defined, a voltage of, for example, 10 V can be preferably used as the applied voltage (corresponding to the amplitude of an alternating voltage). The low voltage is preferably a constant voltage of 0 V or an appropriate alternating voltage of a square wave having the same period as that of the high voltage, and its amplitude (applied voltage) is lower than that of the high voltage.

To calculate the theoretical value to be used in fitting to the measured value of the ON response characteristics, only the rotational viscosity coefficient $\gamma_1$ is varied in calculation. Values of other liquid crystal materials (general values in literatures) are assigned as the initial values of the other viscosity coefficients. In this calculation, Equation 1 and Equation 2 described above are numerically solved to determine the change in transmittance with time, by using the results of calculations of the alignment varying with time. In the case where two polarizers are placed orthogonally to each other, the formula $T=\sin^2(\pi \times \delta/\lambda_0)$, where $\lambda_0$ is the wavelength of light to be measured and $\delta$ is the retardation of a liquid crystal cell, is used to calculate the transmittance T.

In the first step, as described above, the calculation conditions for the calculated values and the measurement conditions for the measured values are matching conditions where the effects of the rotational viscosity coefficient $\gamma_1$, can be independent of those of the other viscosity coefficients. Therefore, the viscosity coefficient $\gamma_1$ determined by fitting the calculated values and experimental values is more accurate than that determined by a conventional fitting procedure.

Next, in the second step, the Miesovicz shear viscosity coefficients $\eta_1$ and $\eta_2$ are determined by fitting the calculated values to the experimental values obtained by measuring the OFF response characteristics of the same liquid crystal cell as that in the first step. The OFF response characteristics are electro-optical response characteristics at the point of OFF switching, that is, when a voltage applied to the liquid crystal cell is switched from a high voltage to a low voltage. The OFF response characteristics can be described as a change in the transmittance of the liquid crystal with time elapsed from the OFF switching. Although the switching direction of the applied voltage in the second step is opposite that in the first step, that is, the direction from the high to low voltages, the forms of the applied voltage and its value at low and high levels can be the same as those in the first step.

Since the effects of the twist viscosity coefficient $\eta_3$ and the compression viscosity coefficient $\eta_{12}$ on the OFF response characteristics are so small as to be negligible, only the Miesovicz shear viscosity coefficients $\eta_1$ and $\eta_2$ are varied to determine the calculated value to be used in fitting to the experimental value, in a similar manner to that in the first step. The rotational viscosity coefficient $\gamma_1$ is fixed at the value determined in the first step, and the twist viscosity coefficient $\eta_3$ and the compression viscosity coefficient $\eta_{12}$ are assigned the same values as those in the first step.

In the second step, as described above, the calculation conditions for the calculated values and the measurement conditions for the measured values are matching conditions where the effects of the Miesovicz shear viscosity coefficients $\eta_1$ and $\eta_2$ can be independent of those of the other viscosity coefficients. Therefore, the Miesovicz shear viscosity coefficients $\eta_1$ and $\eta_2$ determined by fitting the calculated values and experimental values are more accurate than those determined by a conventional fitting procedure.

Moreover, the number of parameters simultaneously varied in calculating the response characteristics is one in the first step and two in the second step, which are smaller than that in the case of the conventional fitting procedure, where as much as four parameters need to be simultaneously varied. Therefore, the time required for calculation is significantly reduces, even allowing for the increased time caused by dividing the calculation procedure into two steps.

If $\eta_1$ and $\eta_2$ temporarily used in the first step differ considerably from the result in the second step, a higher degree of accuracy can be achieved by performing the procedure in the first and second steps again, using $\eta_1$ and $\eta_2$ obtained in the second step.

Figure 2:
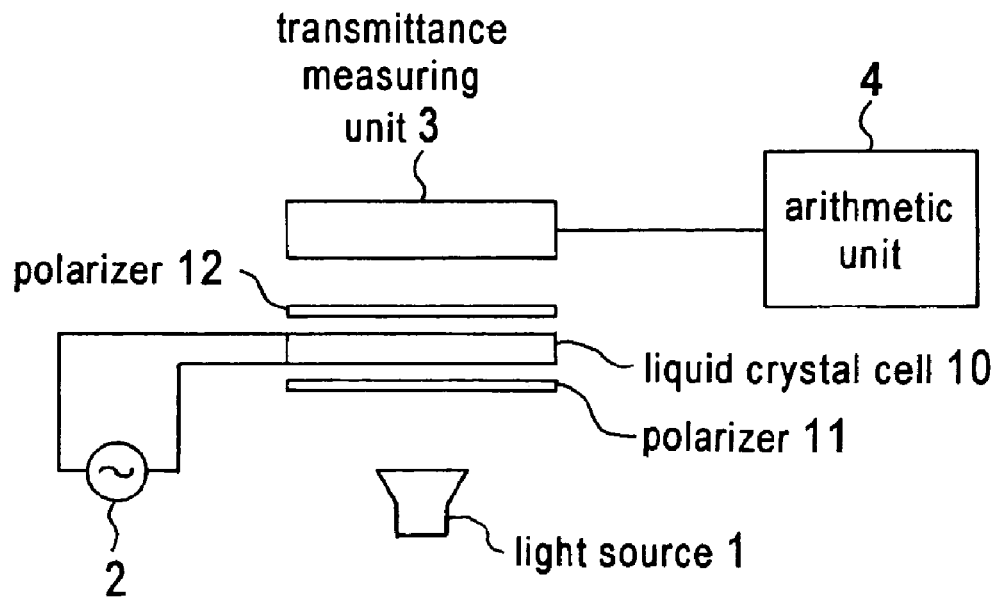
FIG. 2 is a diagram showing a preferred embodiment of a measuring device according to the present invention.

It is preferable that a measuring device, such as that shown in FIG. 2, be used to efficiently implement the measuring method of the present invention. Referring to FIG. 2, a light source 1 illuminating a liquid crystal cell 10 may be any light source, such as a white light source and a monochromatic light source. A polarizer 11 and a polarizer 12 are disposed at the entry side and the exit side, respectively, of the liquid crystal cell 10. A voltage supply 2 may be any voltage supply that is capable of switching the voltage applied to the liquid crystal cell 10 between high and low levels. The voltage supply 2 can be easily composed of a standard two-level power supply and a switching device.

A transmittance measuring unit 3 is preferably capable of collecting transmittance data for light originating from the light source 1 and sequentially passing through the polarizer 11, the liquid crystal cell 10, and the polarizer 12 at intervals of 100 μs or less, from the point at which the applied voltage is switched to a high or low level. This is because if the time intervals of the collection of transmittance data are larger than 100 μs, the time resolution of the transmittance becomes coarse, and the accuracy of fitting may be degraded. The transmittance measuring unit 3 can be formed by combining a light detector, such as a photomultiplier and a photodiode, an A/D converter, and a digital oscilloscope and the like.

An arithmetic unit 4 is preferably a normal computer with a function for performing the fitting operation in two steps of the present invention, on the transmittance data collected by the transmittance measuring unit 3. In the fitting operation in two steps, as described above, a value of the rotational viscosity coefficient $\gamma_1$ is determined by fitting the theoretical values calculated on varying $\gamma_1$, to the transmittance data obtained when the voltage supply 2 is switched to the high level (first step); and values of the Miesovicz shear viscosity coefficients $\eta_1$ and $\eta_2$ are determined by fitting the theoretical values calculated on varying $\eta_1$ and $\eta_2$ while $\gamma_1$ is fixed at the value determined in the first step, to the transmittance data obtained when the voltage supply 2 is switched to the low level (second step).

The switching timing of the voltage supply 2 and the start timing of the data collection by the transmittance measuring unit 3 are preferably under synchronous control. The synchronous control may be performed by a computer, if it serves as the arithmetic unit 4, or by synchronous control means provided separately.

EXAMPLE

Figure 3A:
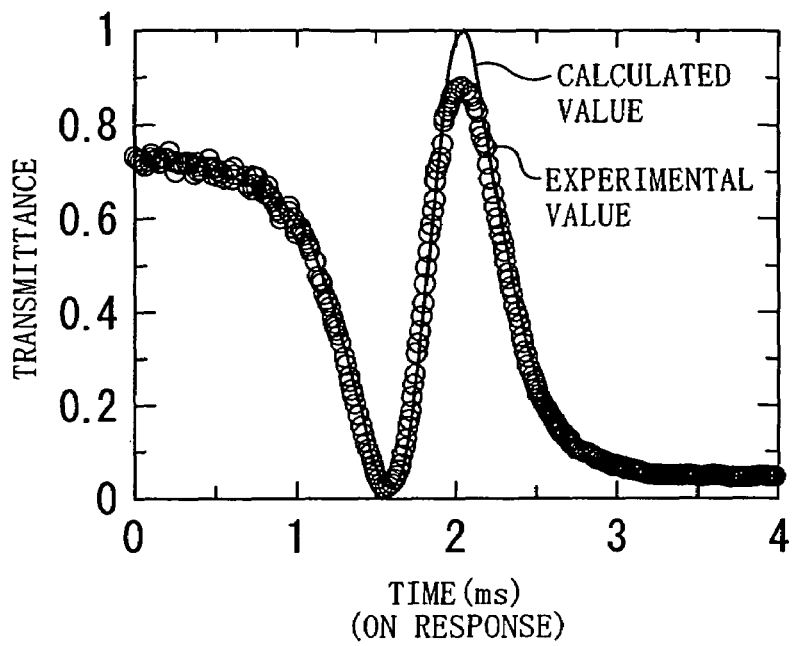
FIG. 3A and FIG. 3B are an ON-response characteristic diagram and an OFF-response characteristic diagram, respectively, showing the results obtained by fitting the experimental values to the calculated values in an example.
Figure 3B:
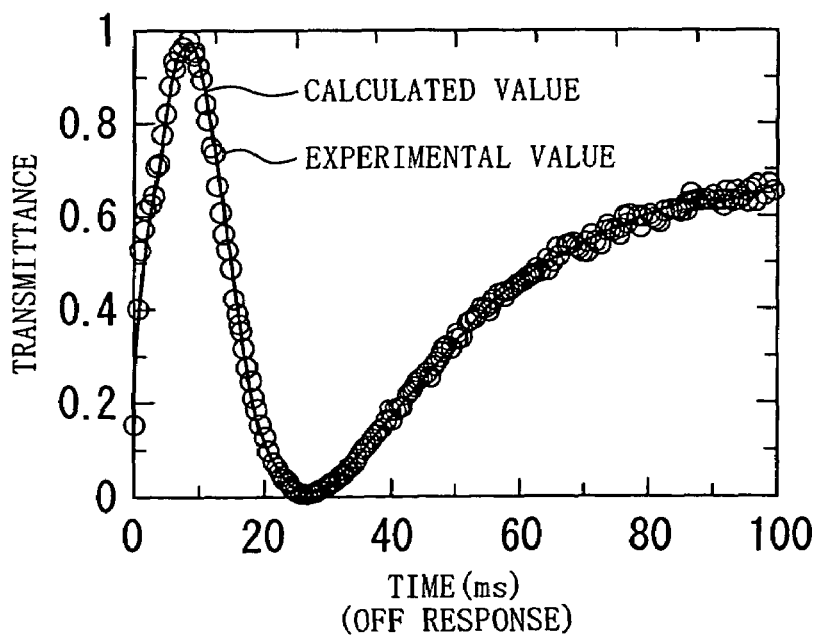

A liquid crystal material TD1016XX (produced by Chisso Corporation), an alignment layer AL1254 (produced by Japan Synthetic Rubber Company Limited) are used to produce a liquid crystal cell (cell gap: 6 μm) with homogeneous alignment, thereby measuring the response characteristics according to the measuring method of the present invention. A measuring device having a structure as shown in FIG. 2 is used. The applied voltage is an alternating voltage of a square wave with a period of 1 ms and an amplitude of 10 V at a higher level, and is a constant voltage 0 V at a lower level. FIG. 3A and FIG. 3B show the result obtained by fitting the experimental values and the calculated values in the first step (ON response: FIG. 3A) and the second step (OFF response: FIG. 3B). The viscosity coefficients determined by the fitting are $\gamma_1$=131 cP, $\eta_1$=145 cP, and $\eta_2$=12 cP, where 1 cP (centipoise)=1 mPa·s.

Figure 4A:
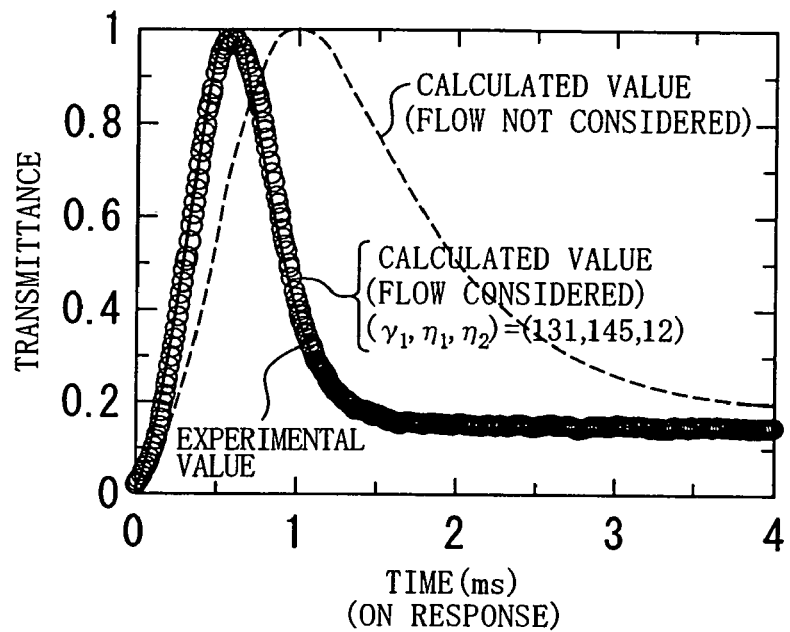
FIG. 4A and FIG. 4B are an ON-response characteristic diagram and an OFF-response characteristic diagram, respectively, showing the comparison between calculated values and experimental values for a liquid crystal cell with bend alignment.
Figure 4B:
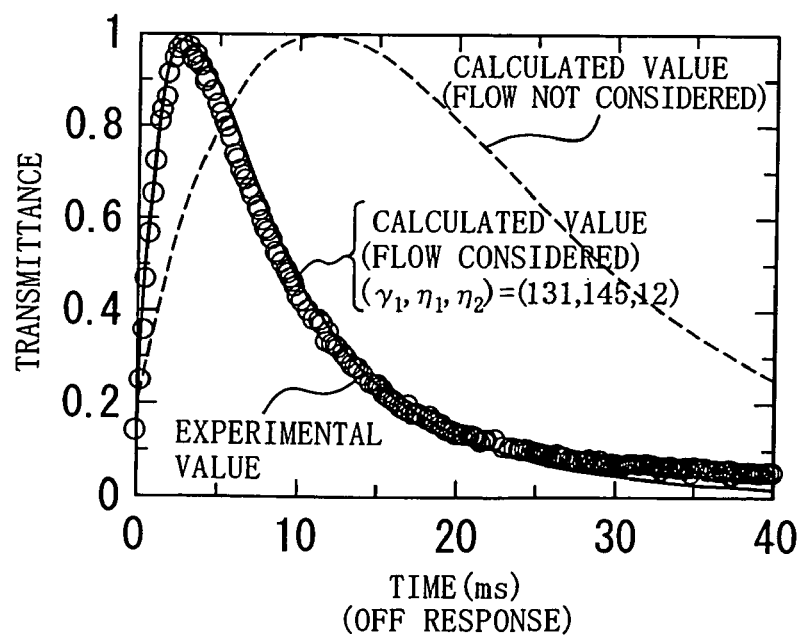

To test the reliability of the values determined, a liquid crystal cell with bend alignment, which is opposite to the homogeneous alignment in terms of the direction of flow effects, is produced to compare the calculated response characteristics with the experimental values. The result is shown in FIG. 4A and FIG. 4B. In FIG. 4A and FIG. 4B showing the ON response characteristics and the OFF response characteristics, respectively, the solid lines indicate calculated values with consideration of the flow using the determined values described above, while the dotted lines indicate calculated values without consideration of the flow. As is obvious from FIG. 4A and FIG. 4B, the calculated values with consideration of flow using the viscosity coefficients measured by the measuring method of the present invention faithfully reproduce the experimental values.

Figure 5A:
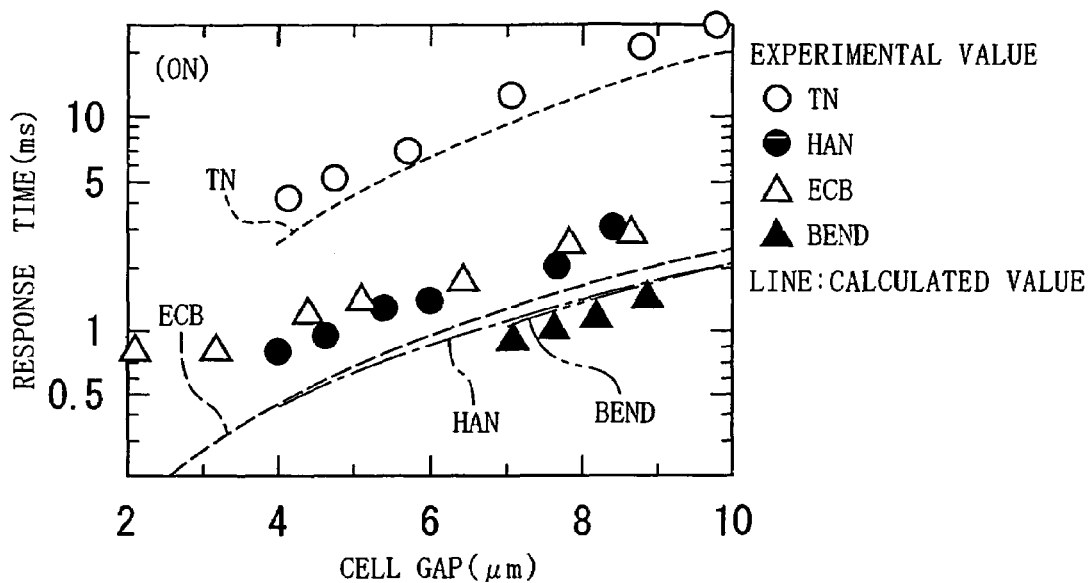
FIG. 5A and FIG. 5B are calculation/experiment comparative diagrams showing the comparison between the cell-gap dependence of the response time calculated without consideration of the flow according to the conventional method, and the experimental values.
Figure 5B:
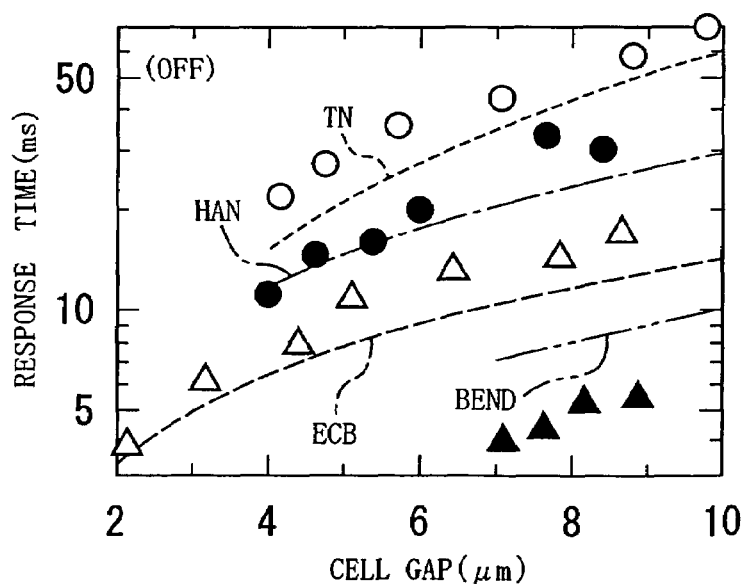
Figure 6A:
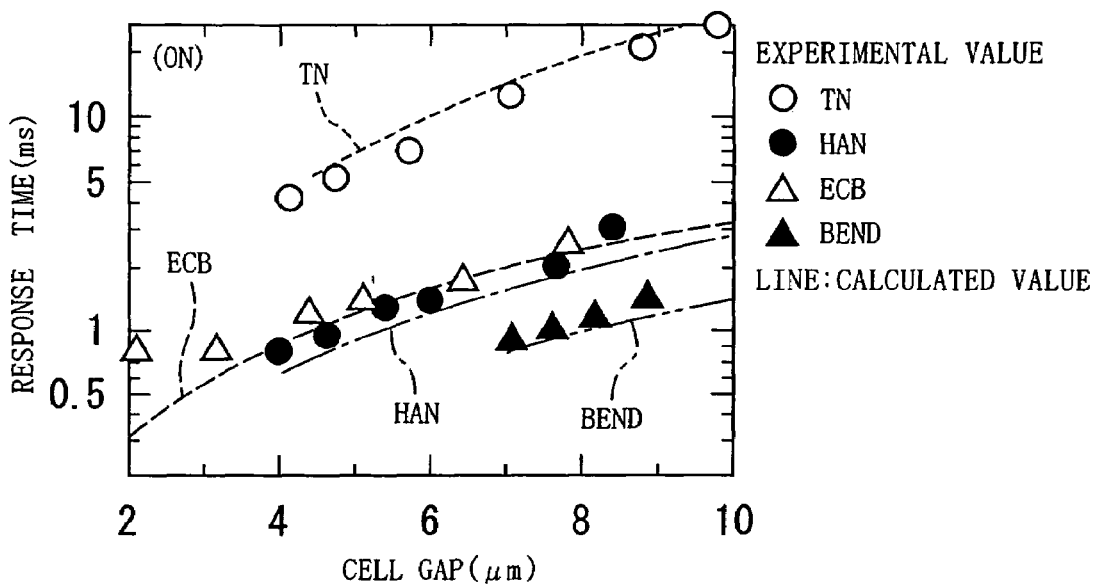
FIG. 6A and FIG. 6B are calculation/experiment comparative diagrams showing the comparison between the cell-gap dependence of the response time calculated with consideration of the flow according to the present invention, and the experimental values.
Figure 6B:
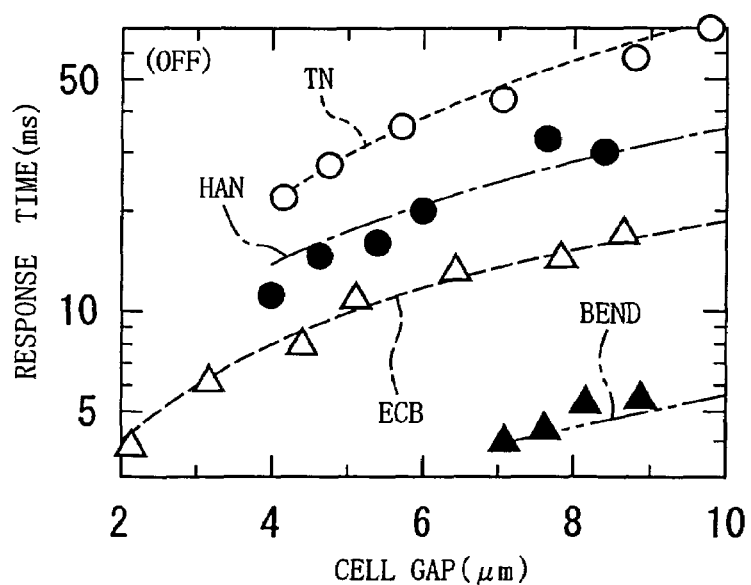

In the calculation without consideration of the flow, for example as shown in FIG. 5A and FIG. 5B, there is no good agreement between the values obtained by calculating the cell-gap dependence of the response time of various types of liquid crystal cells and the experimental values. In addition, the ON response (FIG. 5A) and the OFF response (FIG. 5B) are not consistent in terms of the tendency of disagreement with the experimental values. On the other hand, in the calculation using the viscosity coefficients measured by the measuring method of the present invention with consideration of the flow, for example as shown in FIG. 6A and FIG. 6B, there is much better agreement with the experimental values. In FIGS. 5A and 5B and FIGS. 6A and 6B, TN stands for twisted nematic liquid crystal cell, HAN stands for hybrid aligned nematic liquid crystal cell, ECB stands for horizontally-aligned liquid crystal cells in electric-field control birefringence mode, and BEND stands for liquid crystal cells with bend alignment. The response time for the ON response is the time for the transmittance to rise from 0% to 90%, while the response time for the OFF response is the time for the transmittance to fall from 100% to 10%.

INDUSTRIAL APPLICABILITY

The present invention can be used in industries involved in LCD design, manufacturing, testing, and the like.

The invention claimed is:

1. A measuring method for determining values of viscosity coefficients of a liquid crystal, the measuring method comprising the steps of:
    measuring ON electro-optical response characteristics of a liquid crystal cell with homogeneous alignment when a voltage applied to the cell switches from low to high;
    determining a value of a rotational viscosity coefficient $\gamma_1$ from the measured ON response characteristics;
    measuring OFF electro-optical response characteristics of the liquid crystal cell when the voltage applied to the cell switches from high to low; and
    determining values of Miesovicz shear viscosity coefficients $\eta_1$ and $\eta_2$ from the measured OFF response characteristics.

2. A measuring device for determining values of viscosity coefficients of a liquid crystal, the measuring device comprising:
    a light source illuminating a liquid crystal cell;
    a voltage supply switching a voltage applied to the liquid crystal cell between high and low levels;

a transmittance measuring unit collecting transmittance data for light originating from the light source and passing through the liquid crystal cell, at intervals of 100 μs or less, from a switching point at which the voltage supply switches between the high and low levels; and an arithmetic unit for determining a value of a rotational viscosity coefficient $\gamma_1$ by fitting theoretical values calculated on varying $\gamma_1$ to data collected by the transmittance measuring unit when the voltage supply is switched to the high level, and for determining values of Miesovicz shear viscosity coefficients $\eta_1$ and $\eta_2$ by fitting the theoretical values calculated on varying $\eta_1$ and $\eta_2$, while $\gamma_1$ is fixed at the value previously determined, to data collected by the transmittance measuring unit when the voltage supply is switched to the low level.

3. The method of claim 1, wherein the ON and OFF response characteristics include a change in a transmittance of the liquid crystal over time from when the voltage switches.

* * * * *